Figure 6:
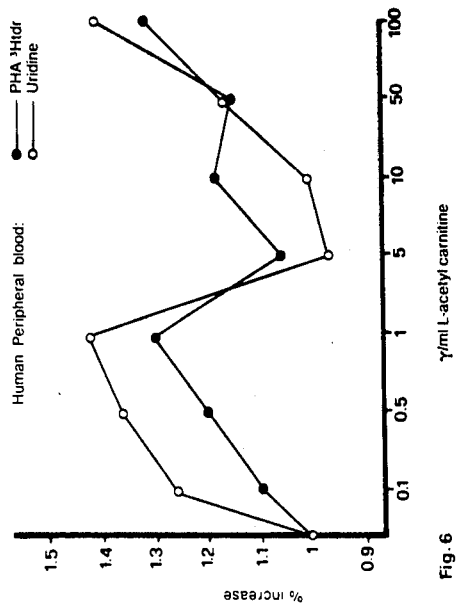

United States Patent [19]

Cavazza

[11] 4,415,588

[45] Nov. 15, 1983

[54] THERAPEUTICAL METHOD OF TREATING PATIENTS WITH IMPAIRED IMMUNE SYSTEM

[75] Inventor: Claudio Cavazza, Rome, Italy

[73] Assignee: Sigma-Tau Industrie Farmaceutiche Riunite S.p.A., Rome, Italy

[21] Appl. No.: 396,279

[22] Filed: Jul. 8, 1982

[30] Foreign Application Priority Data

Jul. 9, 1981 [IT] Italy .............................. 48866 A/81

[51] Int. Cl.³ .................... A61K 31/22; A61K 31/205
[52] U.S. Cl. .................................... 424/311; 424/316
[58] Field of Search .............................. 424/316, 311

[56] References Cited

U.S. PATENT DOCUMENTS 4,194,006 3/1980 Cavazza .............................. 424/312
4,268,524 5/1981 Cavazza .............................. 424/312

*Primary Examiner*—Stanley J. Friedman
*Attorney, Agent, or Firm*—Bruce M Collins

[57] ABSTRACT

In view of the discovery that acetylcarnitine, particularly L-acetylcarnitine, shows immunomodulating activity, a therapeutical method is disclosed for the treatment of patients whose immune system needs to be restored to normal and/or stimulated.

3 Claims, 8 Drawing Figures

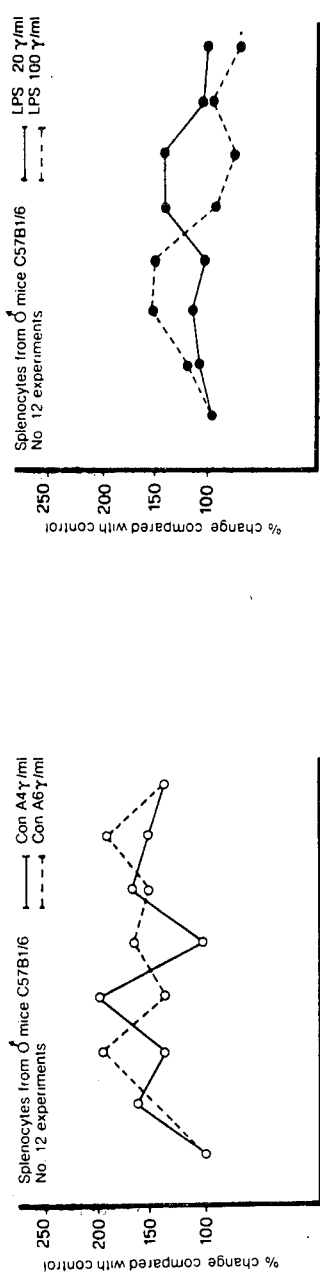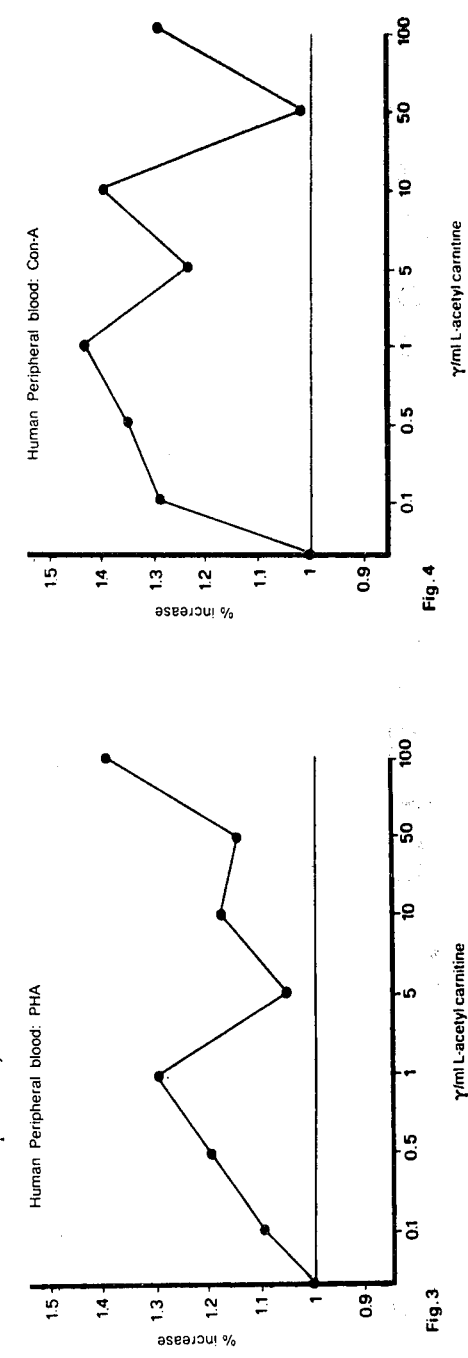

THERAPEUTICAL METHOD OF TREATING PATIENTS WITH IMPAIRED IMMUNE SYSTEM

The present invention relates to a novel therapeutical utilization of acetyl carnitine and, more specifically, relates to the use of acetylcarnitine as immunomodulator.

Acetyl carnitine,

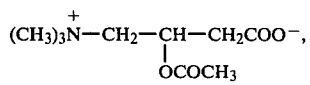

is a known compound, the preparation whereof has been described e.g. by E. Strack et al. in Chem. Ber. 86 525/9 (1953).

Acetylcarnitine contains an asymmetric carbon atom and thus exists in the racemic (D,L) form and in the optically active, dextrorotatory and levorotatory forms.

Hereinbelow, reference will be made for simplicity sake to acetylcarnitine, meaning to include all the three foregoing forms, although L-acetylcarnitine is the most active form.

Previous therapeutical utilizations of acetyl carnitine are already known. for instance, in the U.S. Pat. No. 4,194,006 the use of some acylcarnitines, inter alia acetylcarnitine, is disclosed in the therapeutical treatment of impaired cardiac function, myocardial anoxia and cardiac arrhythmias.

It should be clearly understood that there is no possible relationship between the previously known therapeutical uses of acetylcarnitine and that as immunomodulator. Indeed, it is absolutely surprising that a compound endowed with therapeutical activity in the treatment of cardiac disorders is active as immunomodulator or viceversa. In fact, there is no known theoretical-scientific relationship between the cardiovascular tract and the immune system. For instance, as far as is known, levamisole, methisoprinol and the thymic hormones do not possess a therapeutical activity other than as immunomodulators.

While it is on one hand apparent that it would be advantageous to widen the limited range of immunomodulators nowadays at physician's disposal, on the other hand it should also be noticed that the previously mentioned immunomodulators are not free from untoward side effects. For instance, in Clin. Immunol. Immunopathol 14 70, (1979) allergic reactions have been reported in some patients treated with thymic hormones (thymosin). Thus, thymosin should not be given to patients with histories of allergy, and in general the patients receiving injection of this immunostimulating agent should be strictly monitored by skin testing. Levamisole has a variety of side effects and frequently the patients administered with this immunostimulating agent complain of nausea and flu-like malaise. Cutaneous rashes disappearing after cessation of therapy have been reported. The most serious side effect is granulocytopenia a phenomenon which, although reversible and bound to disappear upon discontinuing therapy, requires that white cell counts be strictly monitored in patients taking the drug for prolonged periods. Moreover, since in Cancer Treat. Rep. 62, 1623 (1978) high concentrations of levamisole have been reported to bring about suppression rather than augmentation of human T cell responses to mitogens, the clinical treatment of patients must include careful immune monitoring to ensure that the immune system is stimulated rather than suppressed. A similar phenomenon is presented also by the thymic hormones (see "Advances in Immunopharmacology", Editors J. Hadden, L. Chedid, P. Mullen, F. Spreafico; Pergamon Press (1981)). Toxicity, teratogenecity and carcinogenicity studies carried out on methisoprinol have shown that this substance is well-tolerated and remarkably free of side effects, even when administered for prolonged periods. However, since methisoprinol molecule contains an inosine moiety, a naturally occurring purine in lymphocytes that is metabolized via normal biochemical pathways to uric acid, hyperuricemia has been noticed.

From the foregoing it is apparent that it would be useful for the physician to have available a novel immunomodulating substance free of the untoward side effects usually presented by the known immunostimulants at present on the market.

Surprisingly, it has now been found that acetylcarnitine, particularly L-acetylcarnitine, is an effective immunomodulating agent which is free of the previously mentioned untoward side effects.

Consequently, the present invention is essentially based on the use of acetylcarnitine as immunomodulating agent.

The present invention relates to an orally or parenterally administrable immunomodulating pharmaceutical composition, comprising:

(a) an amount of acetylcarnitine effective to stimulate the immune system of a patient whose immune system needs to be restored to normal and/or stimulated; and (b) a pharmaceutically acceptable excipient.

The present invention also relates to a therapeutical method for the treatment of patients whose immune system needs to be restored to normal and/or stimulated, which comprises orally or parenterally administering acetylcarnitine to said patients, preferably a daily amount of acetylcarnitine comprised between about 5 and about 50 mg/Kg of body weight.

In practice, acetylcarnitine is orally or parenterally administered in any of the usual pharmaceutical forms which are prepared by conventional procedures well-known to those persons skilled in the pharmaceutical technology. These forms include solid and liquid oral unit dosage forms such as tablets, capsules, solutions, syrups and the like as well as injectable forms, such as sterile solutions for ampoules and phials. When in unit dosage form the composition comprises from about 100 to about 1000 mg of acetylcarnitine.

The immunostimulating properties of acetylcarnitine have been shown by experimental studies carried out on immunocompetent cells drawn from healthy human beings and animals.

Among these studies the following are hereinbelow illustrated:

(A) Studies in mice.
   Influence of acetylcarnitine on the proliferative responses of lymphocytes following mitogenic stimulation "in vitro".
(B) Studies in man.
   1—Influence of acetylcarnitine on the proliferative responses of human lymphocytes following mitogenic stimulation "in vitro".
      (a) DNA synthesis
      (b) RNA synthesis
   2—Influence of acetylcarnitine on leucocytes 3—Influence of acetylcarnitine on glucocorticoid-treated immune cells.

It is well-known that the foregoing tests are worldwide recognized screening tests for assessing the properties of immunosuppressive and immunostimulating substances.

(A) STUDIES IN THE MOUSE

Mitogenic stimulation "in vitro".

The lymphocytes, if suitably stimulated "in vitro" by various substances, undergo blast transformation and proliferation. The agents which evoke proliferation on a nonimmune basis are aspecifically defined as mitogens. Some mitogens selectively stimulate mature and immature T lymphocytes (Con A = concanavaline A), while others (LPS = lipopolysaccharide) are specific for the B cells. The cell proliferation can be suitably monitored by using radioactive tracers such as tritium-labelled thymidine ($^3$Htdr) and then counting the preparations with a betacounter. Because of their selectivity, the mitogens can be of help in the identification of cellular subpopulations sensitive to the action of a specific substance.

The lymphocytes were obtained from the spleens of male mice, strain C57B1/6, weighing 18–20 g. The cells were suspended in sterile culture medium RPMI 1640 with the following additions; 5% serum from fetal calf, 4 mM glutamine and antibiotics. Successively they were spread on microtitre plates with a concentration of $5 \times 10^5$ cells per well. Con A and LPS were used as mitogens at various concentrations (4 and 6 μg/ml, 20 and 100 μg/ml respectively). L-acetylcarnitine was added at doses of 0.1, 0.5, 1, 5, 10, 50 and 100 μg/ml (final concentration) at the beginning of culture. After 72 hours of incubation in 5% $CO_2$ of which the last 18 were in the presence of $^3$Htdr (1 μCi) the plates were aspirated with a Harvester Mash II. The preparations were read successively with a Beckman beta counter and the results were expressed in counts per minute (c.p.m.).

The percent of variation of the cells stimulated with mitogens in the presence of L-acetylcarnitine in respect to the cells stimulated by mitogens is reported graphically in FIGS. 1 and 2. Naturally, the initial radioactivity of the cells incubated with or without substances and without mitogens was subtracted from all the preparations.

L-acetylcarnitine favors the incorporation of $^3$Htdr by the splenocytes stimulated with the mitogens Con A or LPS. The effect is greater for the T lymphocytes in respect to the B lymphocytes. The strengthening effect of L-acetylcarnitine is observable only if it is placed in contact with cells activated with mitogens. This proves that L-acetylcarnitine does not have mitogenic properties and is not capable of inducing the production of mitogenic factors. It is also evident that the immunomodulating action of L-acetylcarnitine is different according to the quantity of mitogen used. This allows us to specify: (a) a facilitating action at determined concentrations of mitogen; (b) an increase in the relative proportion of cells capable of responding to a determined concentration of mitogen. According to the quantity of mitogen used to stimulate the cells, the substance shows an immunomodulating action at different concentrations.

(B) STUDIES IN MAN

1—Mitogenic stimulation "in vitro"

(a) DNA Synthesis

The ability of human lymphocytes to transform themselves in the presence of minimum amounts of certain substances of bacterial and vegetal origin and also of inorganic molecules into blast cells and to proliferate by mitosis in vitro is a well defined characteristic reflecting both the immune status and immune potential of the whole organism in vivo. The lymphocyte transformation is assessed by monitoring the incorporation of DNA of the cell undergoing division of a radioactivity labelled aminoacid, usually tritium-labelled thymidine ($^3$Htdr). The velocity and amount of incorporated isotopes expressed as counts per minute (c.p.m.) by a beta counter reflects the response intensity and is directly proportional to the number of stimulation-respondent cells.

In order to stimulate the lymphocytes, mitogens of vegetal origin have been used. Phytohaemagglutinin (PHA) and concanavalin (Con A) act on T-lymphocytes even though participation to proliferative responses of B-cells can not be excluded, whereas PWM (mitogen extracted from American phytolacca) acts on both T- and B-lymphocytes.

It is known that lymphocytic stimulation tests are a useful means for assessing the influence of a substance on the immune responses "in vitro". Indeed, an increased response after mitogen stimulation in the presence of a substance whose immune effect is under study can be ascribed to the substance itself and precisely to: (1) an increase in the relative proportion of the cells able to respond to the utilized mitogens; (2) a response triggered to specific concentrations of a certain mitogen; (3) an amplification of the phenomenon once it has started; (4) a larger involvement of accessory cells such as macrophages and/or some lymphocyte subpopulations.

To carry out this test lymphocytes isolated from peripheral blood of ten healthy donors of either sex according to the previously described procedures were used. After checking their vitality, the cells were counted and brought to the concentration of $1 \times 10^6$ cells/ml in RPMI 1640 to which 20% of decomplemented AB serum had been added. 100 μl of the cell suspension were spread on flat-bottomed microtiter plates and incubated in the presence or absence of PHA (6 γ/ml), Con A (10 γ/ml) or PWM (6 γ/ml), with or without L-acetyl carnitine at the concentrations of 0.1-0.5-1-5-10-50-100 μg/ml for 72 hours in a 5% $CO_2$ atmosphere, at 37° C. Tritium-labelled thymidine (1 μCi per well) was added 16 hours before culture termination. The plates were aspirated by an automatic apparatus (Harvester Mash II). Radioactivity was assessed by a beta counter (Beckmann). Each result is the average of ten tests carried out individually in triplicate.

Figure 5:
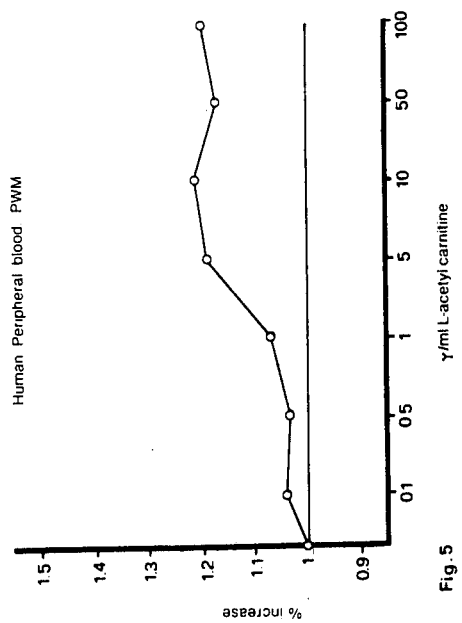

The results obtained are plotted in FIGS. 3, 4 and 5. The addition of L-acetyl carnitine at different concentrations to the wells does not bring about any significant effect if the cultures have not been stimulated by mitogens. This shows that L-acetyl carnitine does not possess mitogenic properties. In the presence of PHA, L-acetylcarnitine enhances DNA synthesis at the concentrations of 1 μg/ml and 100 μg/ml and in a statistically signifincant way. If lymophocyte cultures are stimulated with Con A, the enhancing effect reaches its peak at 1 and 10 μg/ml. Conversely, PWM-incubated cells are slightly affected by L-acetylcarnitine and the percentage increase does not exceed 22%.

As can be seen from the attached figures, L-acetyl carnitine immunomodulating effect shows up at different concentrations with a typical double-peak pattern. This phenomenon has been already described in connection with other immunomodulant drugs and can likely be attributed to distinct cell subpopulations showing distinct sensitivities to different concentrations of the substance or to the fact that it can display different actions depending on the employed concentrations.

The results obtained by the applicant confirm the results previously obtained with murine lymphocytes in an "in vitro" similar system: L-acetylcarnitine acts on T-lymphocytes and also on human B-lymphocytes.

(b) RNA Synthesis

After mitogenic activation and before DNA synthesis becomes detectable, lymphocytes incur a whole series of metabolic modifications, RNA synthesis among others.

Similarly to what has been shown for DNA synthesis, also RNA synthesis can be suitably monitored, after mitogenic stimulation, by using a radioactive tracer, in this case tritium-labelled uridine ($^3$H-uridine). It has been shown that RNA synthesis starts immediately after mitogen stimulation and that after 20 hours from PHA stimulation RNA increase is about twice as much the initial amount.

Both the information RNA (messenger RNA and high molecular weight RNA) and the structural RNA (ribosomial RNA and transfer RNA) increase, however the informational RNA, having a higher turnover, is responsible for most of the newly formed synthesis RNA.

The purpose of this test is to assess the effect of L-acetyl carnitine at the final concentrantions of 0.1-0.5-1-5-10-50-100 μg/ml on RNA synthesis by human lymphocytes stimulated with PHA.

The method for assessing RNA synthesis by human lymphocytes obtained by healthy donors is substantially the same as that previously described for DNA synthesis, except that cells are cultured for 12 hours, the last three hours in the presence of $^3$H-uridine.

The results plotted in FIG. 6 show that L-acetyl carnitine is able to promote RNA synthesis by PHA-stimulated lymphocytes. On the grounds of present knowledge, the increase is attributable to informational RNA (messenger and high molecolar weight RNA) rather than to structural RNA. Since the lymphocytes stimulated by PHA in the presence of L-acetylcarnitine, and assayed for DNA and RNA synthesis, show the activation peaks which are substantially superimposable, it can be stated that L-acetylcarnitine induced immunomodulation takes place through an increased RNA synthesis, which subsequently also effects DNA synthesis.

2—Effect on Leucocytes

It is known that several clinical and experimental studies have shown that leucocyte motility is of importance in the complex defence mechanisms of the host against pathogenous agents. Indeed, a suitable cell number is not sufficient by itself to protect the organism if they are not located at the inflammatory sites. During infections and/or when some tissue damage occurs, leucocytes refrain from moving in an apparently haphazard way and stop at the lesion site. The mechanism accounting for these cells to react to chemotactic gradients is still unclear. Undoubtedly, the motility stimulus is a multi-step phenomenon that, since it involves the cyclic nucleotides, a number of enzyme reactions, Na, K, ATPase and induces modifications in microtubules and microfilaments, can be modulated at different levels involving;

(a) spontaneous migration
(b) direct migration.

The neutrophilic leucocytes were isolated from the peripheral blood of healthy donors and assayed in a test migration under agarose.

Figure 7:
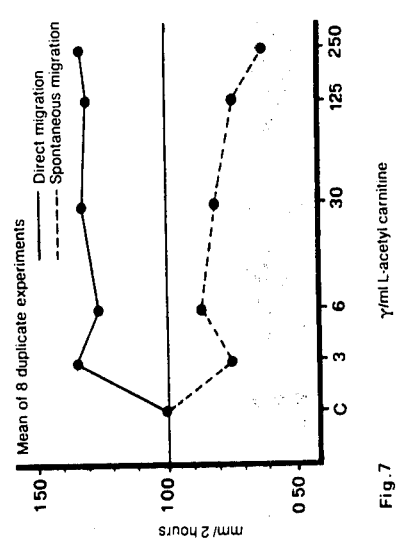

Following cell incubation with different L-acetyl carnitine concentrations (from 3 to 250 μg/ml), it has been possible to evidentiate a stimulation of the direct leucocyte motility. Also spontaneous migration is influenced positively by L-acetyl carnitine, particularly at the doses of 6 and 30 μg/ml. L-acetyl carnitine is able to increase not only the linear distance run by the cells in the presence of the stimulus (in case of direct migration) or in the absence of the stimulus (in case of spontaneous migration), but increase also the number of migrating cells. The results are summarized in the Table and plotted in FIG. 7.

Studies carried out in rats have shown that spermatozoa motility in the seminal duct is proportional to the acetyl carnitine content in seminal fluid. Acetyl carnitine is, apparently, the most important energy-releasing substrate for spermatozoa motility. The studies carried out by the applicant have shown that L-acetyl carnitine stimulates leucocyte motility, both that toward a chemotactic gradient and spontaneous motility. This phenomenon takes place, with varying intensity, in a wide dose range (from 3 to 250 μg/ml), bringing about an increase in both the number of migrating cells and the linear distance run by the cells. L-acetyl carnitine, by favoring transportation of acyl groups across the mitochondrian inner membrane, can by hypothesized to release extra energy, thus facilitating leucocyte motility.

TABLE

| | Direct and spontaneous leucocyte migration | |
|---|---|---|
| L-acetyl carnitine | Direct migration (cells number) | Spontaneous migration (cells number) |
| 3 μg/ml | 370 ± 34 | 185 ± 21 |
| 6 μg/ml | 330 ± 41 | 180 ± 29 |
| 30 μg/ml | 450 ± 46 | 243 ± 18 |
| 125 μg/ml | 487 ± 53 | 225 ± 31 |
| 250 μg/ml | 354 ± 41 | 260 ± 29 |
| Control | 225 ± 38 | 164 ± 19 |

3—Effect on glucocorticoid treated cells

Corticosteroid hormones exert multiple activities on various target tissues and organs. In some cases these hormones induce protein synthesis (anabolic effect), and in other cases they repress genetic transcription or activate inhibitory protein molecule synthesis (antianabolic effect). In the immune system it has been observed that in vitro incubation of murine thymocytes in the presence of $10^{-6}$ M hydrocortisone leads to rapid cell lysis. By contrast, the lymphoid cells in man are corticoresistant, except in certain experimentally induced conditions or during autoimmune diseases. These data suggest that activated T cells are to some degree susceptible to glucocorticosteroids and, therefore, therapeutic efficacy of such drugs is partly accounted for. The purpose of the experiments conducted by the applicant was that of assessing a possible synergism of L-acetyl-carnitine with glucocorticoids.

Figure 8:
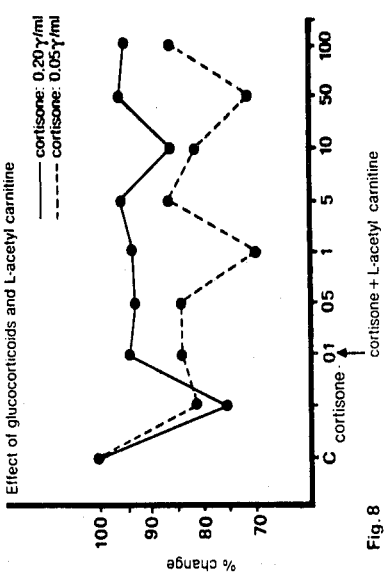

The lymphocytes were isolated from the peripheral blood of healthy donors of either sex and cultured for 6 days (bidirectional mixed cultures). The cells ($10^6$/ml) were then transferred to flat-bottomed microtiter plates and incubated with or without hydrocortisone in the presence or absence of L-acetyl-carnitine at 0.1-0.5-1-5-10-50-100 μg/ml for 20 hours at 37° C. in 5% $CO_2$. The susceptibility to glucocorticosteroids was assessed by scoring the cell lysis. Hydrocortisone was used at the concentrations of 0.20 and 0.05 mg/ml; such concentrations are deemed to be optimal for this type of experiment. The results are reproduced in the form of a graph in FIG. 8.

What is claimed is:

1. The method of stimulating the immune system of living animals by enhancing mitogenic stimulation, B- and T-lymphocyte cooperation, and cell chemotaxis which comprises orally or parenterally administering to an animal in need of such enhancement an effective amount of acetylcarnitine.

2. The method of claim 1 which comprises daily administering from about 5 to about 50 mg of acetylcarnitine per Kg of body weight.

3. The method of claim 2 wherein said acetylcarnitine is L-acetylcarnitine.

* * * * *